United States Patent [19]
Little

[11] Patent Number: 6,055,872
[45] Date of Patent: May 2, 2000

[54] PUSH-PULL VALVE FOR GAS SAMPLING BAGS

[75] Inventor: Stephen R. Little, Parkland, Fla.

[73] Assignee: Jensen Wert Products, Coral Springs, Fla.

[21] Appl. No.: 09/031,823

[22] Filed: Feb. 27, 1998

[51] Int. Cl.[7] ....................................................... G01N 1/12
[52] U.S. Cl. ........................... 73/864.63; 383/44; 141/68
[58] Field of Search ................................. 383/44; 141/68, 141/315; 73/864.63, 864.62, 864.91, 864.64, 864.65, 864.66, 864.51, 864

[56] References Cited

U.S. PATENT DOCUMENTS 5,456,126  10/1995  Suddath ................................ 73/864.63

*Primary Examiner*—Max Noori
*Attorney, Agent, or Firm*—Shoemaker and Mattare, Ltd.

[57] ABSTRACT

A push-pull valve for gas sampling is formed by assembling a body including a receptacle having a bore and a plug having a nose which seats in the bore. The plug has a through bore with a shoulder at its lower end serving as a lower stop and defining a hole at the bottom of the through bore. A hollow stem slides in the through bore, between an extended, closed position, and a retracted, open position. The stem has ports set above the foot of the stem a distance such that, in an upper position of the stem, the port is blocked by an O-ring, and in a lower position of the stem, gas can flow through the stem, the ports, an annular space around the stem, and out through the hole at the bottom of the through bore.

5 Claims, 2 Drawing Sheets

FIG. I

PUSH-PULL VALVE FOR GAS SAMPLING BAGS

BACKGROUND OF THE INVENTION

This invention relates to a push-pull valve for gas sampling bags, which are used to collect samples of potentially toxic gas. Such bags may be used to capture gas samples at toxic waste sites, industrial stacks, or landfills, and may have medical applications as well.

Because the concentration of toxic gases in samples may be very low, the sampling bag has to be clean, and empty initially. It is important to prevent ambient air and other gases from entering the bag before the sample is taken, and even more important to prevent leakage of the sample from the bag.

A test procedure may require the taking of hundreds of samples, so it is important that filling a bag with a gas sample be a simple, quick operation. Valves are typically installed on such bags to permit the tester to open, fill, and then seal the bag. The valve must be reliable, and in addition, inexpensive, again because of the number of bags which must be used. In most cases, the valve and bag will be used only once before disposal.

Prior inventors have proposed valves having a hollow stem which can be pulled or pushed, rotated or hinged to either close or open the valve. Some such valves have been used on gas sampling bags.

SUMMARY OF THE INVENTION

An object of the invention is to provide an inexpensive, reliable push-pull valve for a gas sampling bag.

Another object of the invention is to provide a gas sampling bag valve with a septum which can be punctured by a syringe needle so that one can access the contents of the bag without reopening the valve.

These and other objects are attained by a push-pull valve for gas sampling bags as described in detail below. Briefly, the valve is formed by assembling a body including a receptacle having a bore and a plug having a nose which seats in the bore. The plug has a through bore with a shoulder at its lower end serving as a lower stop and defining a hole at the bottom of the through bore. A hollow stem slides in the through bore, between an extended, closed position, and a retracted, open position. The stem has ports set above the foot of the stem a distance such that, in an upper position of the stem, the port is blocked by an O-ring, and in a lower position of the stem, gas can flow through the stem, the ports, an annular space around the stem, and out through the hole at the bottom of the plug.

BRIEF DESCRIPTION OF THE DRAWINGS

In the accompanying drawings.

DESCRIPTION OF THE PREFERRED EMBODIMENT

Figure 1:
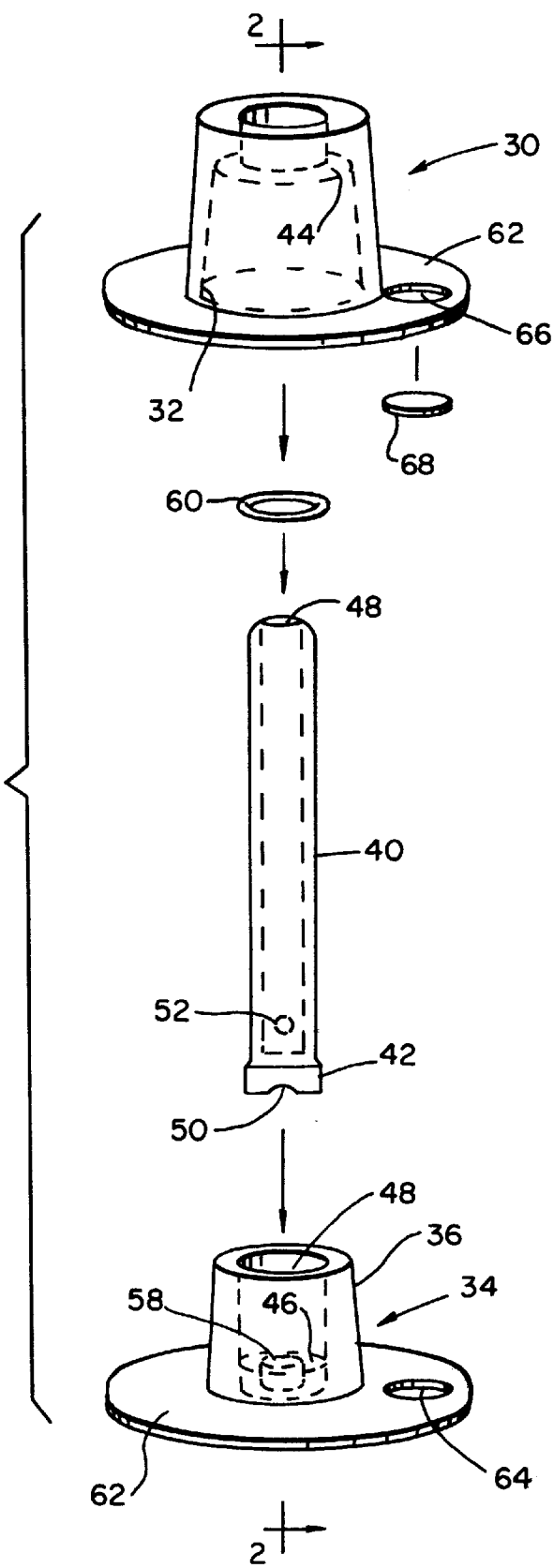
FIG. 1 is an exploded perspective view of a push-pull valve embodying the invention.
Figure 2:
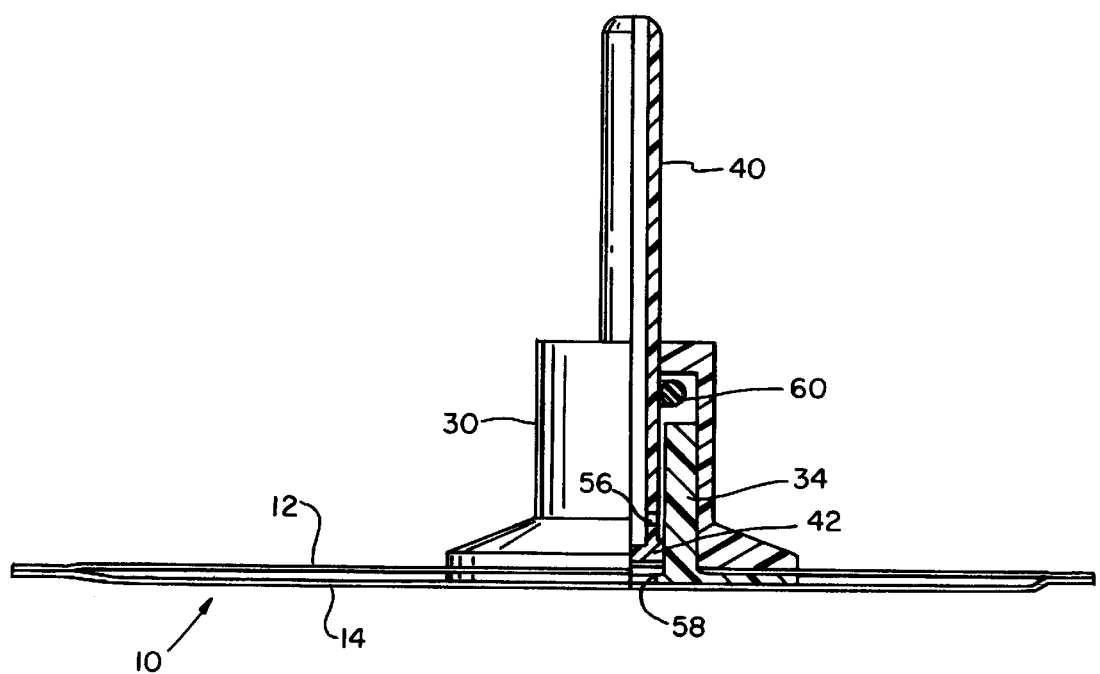
FIG. 2 is a sectional view of the valve taken on the plane 2—2 in FIG. 1.

FIG. 1 shows a valve embodying the invention. It is assembled to a gas sampling bag 10, FIG. 2, made of two sheets 12,14 of "Tedlar", a polyvinyl fluoride film, or Teflon PEP film both made by DuPont. The edges of the bag are sealed along their edges by welding to form a closed volume.

Before the sealing is done, the valve is installed through an aperture formed in the upper sheet, 12. The valve comprises a hat-shaped receptacle 30, having an internally tapered bore 32, and a round plug 34, having a nose 36 which is externally tapered so as to seat within the receptacle's bore. The receptacle and plug are assembled on opposite sides of the sheet 12, tightly sandwiching it so that gas cannot leak around the valve. The taper angle is about 2°, which produces high radial contact forces between the parts when they are pushed together. The forces are sufficient to prevent accidental disassembly, obviating the need for a pin, fastener, adhesive or welding to keep the assembly together.

Before the receptacle and plug are assembled, a hollow stem 40, having a foot 42 which serves as a stop, is inserted upward through the bore 32 of the receptacle 30. Internal shoulders 44,46 on the receptacle and plug, respectively, limit the stroke of the stem by engaging the foot, which is too large to pass either shoulder. The stem can slide lengthwise until the foot engages one shoulder or the other. The stem's bore 48 is closed at the bottom end by the foot 42. Two lateral ports 52 allow gas to move between the stem bore 48 and the annular space 56 defined between the bore 32, the stem 40, and the shoulders 44,46. The annular space then communicates with the interior of the bag via the hole 58 in the center of the plug 34. The arch 50 on the bottom of the foot 42 keeps the bottom surface of the foot from blocking the hole.

The stem is surrounded by an O-ring 60 which has a snug sliding fit on the stem, and is confined between the top of the nose of the plug and the top of the bore of the receptacle. The O-ring is preferably made of buna rubber or "Viton", depending on the degree of cleanliness required. It provides a reliable and simple seal, avoiding a need for other sealing parts.

When the stem is in its uppermost position, the ports 52 lie above the O-ring and thus are isolated from the hole 58, so no gas can pass through the valve. When the stem is pushed to its bottom position, the ports are below the O-ring, and gas can flow through them and to/from the hole 58 via the annular clearance space between the stem and the through bore 32, thence the interior of the bag. The flow path is indicated by arrows in FIG. 2.

The receptacle and plug portions of the valve each have a broad brim 62, and each brim has a through hole (64,66, respectively). The valve is assembled with these holes in alignment. A puncturable rubber septum 68 is installed in a bottom counterbore in the upper hole 66, so that, when the valve is assembled, the septum is confined in the counterbore, and blocks flow through the holes. The septum is slightly thicker than the counterbore is deep, so that the septum bears against the bag wall when the valve is assembled on the bag. One can puncture the septum 68 (and the sheet 12) with the needle of a syringe in order to remove part of the sample, or to introduce reactants. The septum is preferably made of a silicone rubber, and may have a Teflon film facing to reduce contamination. The preferred diameter of the septum is about one-eighth of an inch, which makes a sufficiently large target for the syringe needle, while minimizing the use of rubber material.

In use, an initially empty bag is filled by pushing tubing from a sample source onto the end of the stem and pumping the sample into the bag. The stem is then pulled out, closing the valve, and the tubing is removed. The filled bag is transported to a laboratory, where the needle of an empty syringe is inserted through the septum on the base of the valve, into the bag volume. A portion of the sample is withdrawn into the syringe, and the septum re-closes after the needle is removed. The syringe is then attached to an instrument such as a gas chromatograph, and the sample is analyzed.

Since the invention is subject to modifications and variations, it is intended that the foregoing description and the accompanying drawings shall be interpreted as only illustrative of the invention defined by the following claims.

I claim:

1. A push-pull valve for installation in an aperture in a wall of a gas sampling bag, said valve comprising a body including a receptacle adapted to engage one side of the wall and having a bore and a plug having a nose which seats in the bore when the plug is inserted into the receptacle through the aperture from an opposite side of the wall, the plug having a through bore with a shoulder at its lower end serving as a lower stop and defining a hole at the bottom of the through bore, a hollow stem having a sliding fit in said through bore and being axially movable in the bore between an upper position and a lower position, said stem having a foot at its lower end which engages said shoulder in the lower position of the stem, an O-ring disposed in an annular space defined between said receptacle bore and said stem, said stem having at least one lateral port set above said foot a distance such that, in the upper position of the stem, the port is blocked by the O-ring, and in the lower position of the stem, gas can flow through the stem, the ports, the annular space and the hole at the bottom of the through bore into the bag.

2. The invention of claim 1, wherein the valve further comprises a septum through which one can insert a syringe needle to contact the contents of the bag.

3. The invention of claim 1, wherein each of the receptacle and plug has a brim, and each brim has a hole through it, said holes being aligned during assembly of the valve, and at least one of said holes containing a septum which can be pierced by a syringe needle.

4. The invention of claim 3, wherein the hole in the brim of the receptacle has a counterbore, and the septum is installed in said counterbore.

5. The invention of claim 4, wherein the counterbore faces the brim of the plug, so that the septum is captured in the counterbore by the plug when the valve is assembled.

* * * * *

UNITED STATES PATENT AND TRADEMARK OFFICE
CERTIFICATE OF CORRECTION

PATENT NO. : 6,055,872
DATED : May 2, 2000
INVENTOR(S) : Stephen R. Little

It is certified that error appears in the above-identified patent and that said Letters Patent is hereby corrected as shown below:

Please change the assignee name from "Jensen Wert Products" to --"Jensen Inert Products--.

Signed and Sealed this

First Day of May, 2001

Attest:

NICHOLAS P. GODICI

Attesting Officer      Acting Director of the United States Patent and Trademark Office